United States Patent
Szymaitis

(10) Patent No.: US 6,705,865 B1
(45) Date of Patent: Mar. 16, 2004

(54) DENTAL HAND INSTRUMENT

(76) Inventor: Dennis W. Szymaitis, 1172 Harvard Rd., Pittsburgh, PA (US) 15205

( * ) Notice: Subject to any disclaimer, the term of this patent is extended or adjusted under 35 U.S.C. 154(b) by 160 days.

(21) Appl. No.: 10/082,897

(22) Filed: Feb. 26, 2002

(51) Int. Cl.$^7$ .................................. A61C 3/00
(52) U.S. Cl. ....................................... 433/141
(58) Field of Search .................. 433/141, 142, 433/143, 144, 148, 81, 165, 216, 140; D24/152, 154

(56) References Cited

U.S. PATENT DOCUMENTS

| | | | |
|---|---|---|---|
| 532,721 A | 1/1895 | Dennis | |
| 1,369,582 A | 2/1921 | Wagner | |
| 1,605,320 A | * 11/1926 | Bates | 433/143 |
| 2,479,645 A | 8/1949 | Silverstein | |
| 2,677,843 A | * 5/1954 | Goodman | 15/236.08 |
| 3,625,517 A | * 12/1971 | Durnack | 473/313 |
| 4,643,677 A | 2/1987 | Kim | |
| 4,854,867 A | * 8/1989 | Meinershagen | 433/40 |
| 5,088,925 A | 2/1992 | Mason | |
| D427,681 S | 7/2000 | Maissami | |
| 6,309,219 B1 | * 10/2001 | Robert | 433/144 |
| 2003/0022131 A1 | * 1/2003 | Kangasniemi et al. | 433/147 |

OTHER PUBLICATIONS

Pages 279–283 and 416 of the Fall 1999/Winter 2000 Sullivan–Schein Dental, Dental Merchandise Catalog.

* cited by examiner

Primary Examiner—Kevin Shaver
Assistant Examiner—Melba Bumgarner
(74) Attorney, Agent, or Firm—Buchanan Ingersoll, P.C.

(57) ABSTRACT

A hand-held dental instrument has an elongated handle and a blade shaped like a human foot. The blade has ankle, arch and instep edges that curve inwardly and are of different depth and curvature. There is a shank portion between the blade and the handle with the angles between the shank and the handle and between the shank and the surface of the blade preferably being 150° and 120° respectively. These angles allow the user to reach all areas of the mouth. The blade is thin enough to allow the instrument to reach between the lower front teeth.

19 Claims, 2 Drawing Sheets

DENTAL HAND INSTRUMENT

FIELD OF INVENTION

The invention relates to hand instruments used by dentists and dental hygienists.

BACKGROUND OF THE INVENTION

Dentists use a variety of hand held instruments to place and remove material from teeth and gums. These instruments can be generally classified as carvers, filling instruments and placement instruments. Such instruments have an elongated, generally cylindrical handle and a working tip at one end or both ends. A variety of tips are available ranging from sharp wire tips to flat rounded spatula tips to blunt cylindrical tips. Generally, each tip is shaped to perform a particular function in examining or treating teeth. Wagner in U.S. Pat. No. 1,369,582 discloses a dental tool in which the tip is formed by an angular extension from the handle that is bent to form a rounded heel and terminates in a rounded, gradually tapered point. This tip is designed for manipulating, shaping and burnishing fillings and also wax used in taking wax impressions. U.S. Pat. No. 4,643,677 discloses a dental instrument having an elongated straight handle portion with a cylindrical plugger element on each end thereof. Each plugger element has a 45 degree bend adjacent the end of the handle and a 90 degree bend adjacent the distal end of the plugger element. Protruding laterally from the apex of each 90 degree bend is a burnishing element. The burnishing element on one end of the handle is ball shaped and the burnishing element on the other end is cone-shaped. This instrument is designed for placement and shaping of amalgam filling material. Mason discloses a hand held dental instrument having a ring at each end in U.S. Pat. No. 5,088,925. The ring is designed to be placed in contact with palatal tissue and serve as a guide for a needle that is inserted through the ring into the very center of the palatal tissue. These instruments and the many other dental hand instruments that have been available over the years were designed for specific purposes. They are quite useful for the limited purposes for which they were designed. Because of their limited scope there are many procedures in which several hand instruments must be used. There is a need for a dental instrument that is more versatile.

There is a pocket between the gingiva and the tooth. In a healthy tooth this pocket is very shallow, typically one to three millimeters. Bacteria colonize the pocket. This bacteria causes the pocket to deepen. As periodontal disease progresses the bacteria cause inflammation that destroys the ligament and bone creating depressions in the bone. I have developed a procedure in which certain materials are placed in the periodontal pocket to treat periodontal disease. During this procedure it is often necessary to pack gauze into the periodontal pocket. There are several hand dental instruments that I have used for this purpose. However, none of them has been entirely satisfactory. Many dental instruments have curved tips, but the curvature does not match the curvature of a patient's teeth or the tip does not have a flat surface that can be used to press gauze into the periodontal pocket. Consequently, there is a need for a hand held dental instrument having a tip that contains curved edges matching the curvature of a patient's teeth and a surface and thickness that enables the instrument to be used to press gauze into the periodontal pocket and between the teeth.

SUMMARY OF THE INVENTION

I provide a dental instrument having an elongated handle and a tip at one or both ends. The tip is a blade having a top surface, a bottom surface, opposite the top surface with contoured edges forming a shape similar to a human foot. Consequently, for ease of understanding portions of the edges of the blade are identified with reference to the human foot. A curved ankle edge extends from the handle to a heel shaped edge. The heel edge curves outward until meeting an arch edge. A toe edge extends from the arch edge, the toe edge having a V-shape with a rounded point. An instep edge extends from the toe edge to the handle. The ankle, arch and instep edges each have an inwardly curved shape. The curved shapes are of different depth and concavity. There is a shank portion between the blade and the handle with the angles between the shank and the handle and between the shank and the blade preferably being 150° and 120° respectively. These angles allow the user to reach all areas of the mouth. The blade is thin enough to allow the instrument to reach between the lower front teeth.

these and other advantages and features of the present invention will become more fully understood upon reference to the accompanying drawings illustrating certain presently preferred embodiment of the invention.

DESCRIPTION OF THE PREFERRED EMBODIMENTS

Figure 1:
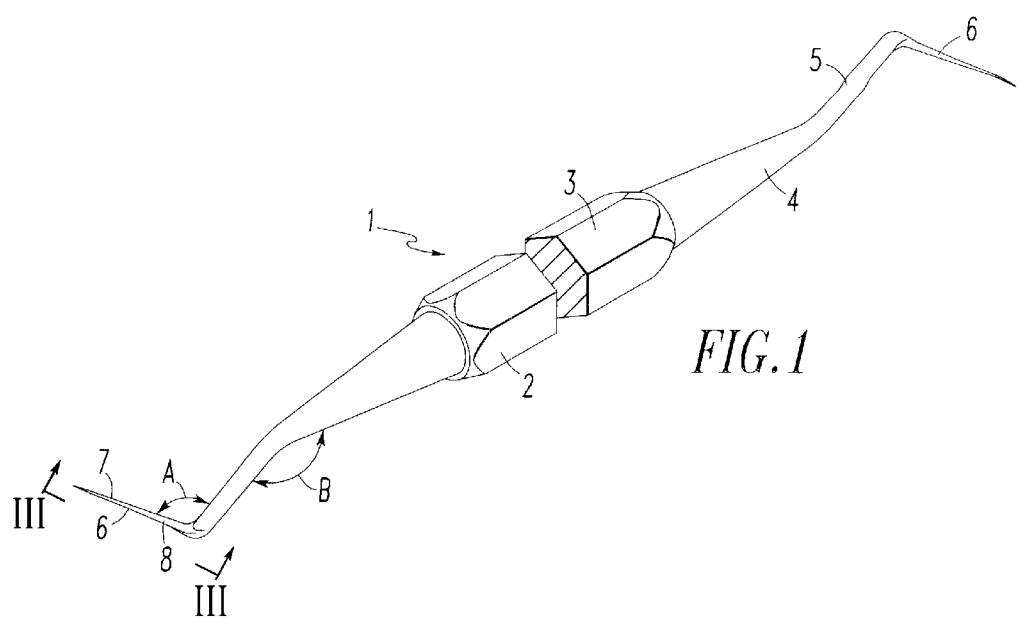
FIG. 1 is a perspective view of a first present preferred embodiment of my dental instrument.
Figure 2:
FIG. 2 is a back view of the dental instrument shown in FIG. 1.
Figure 3:
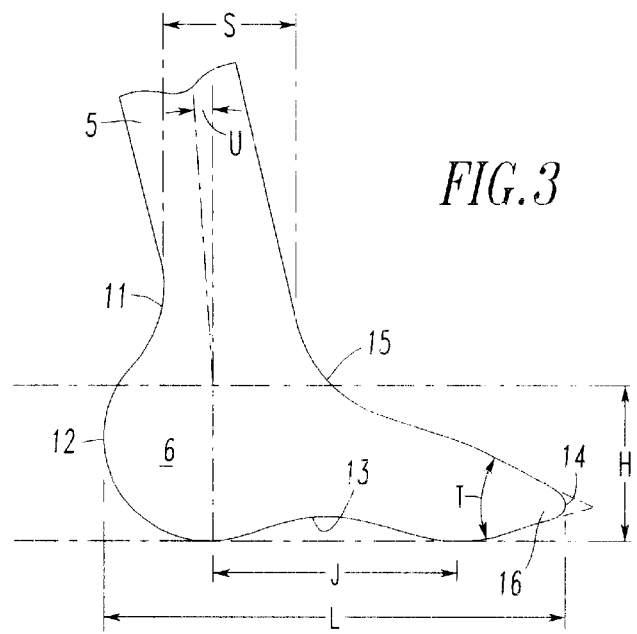
FIG. 3 is an end view taken along the line III—III in FIG. 1.
Figure 4:
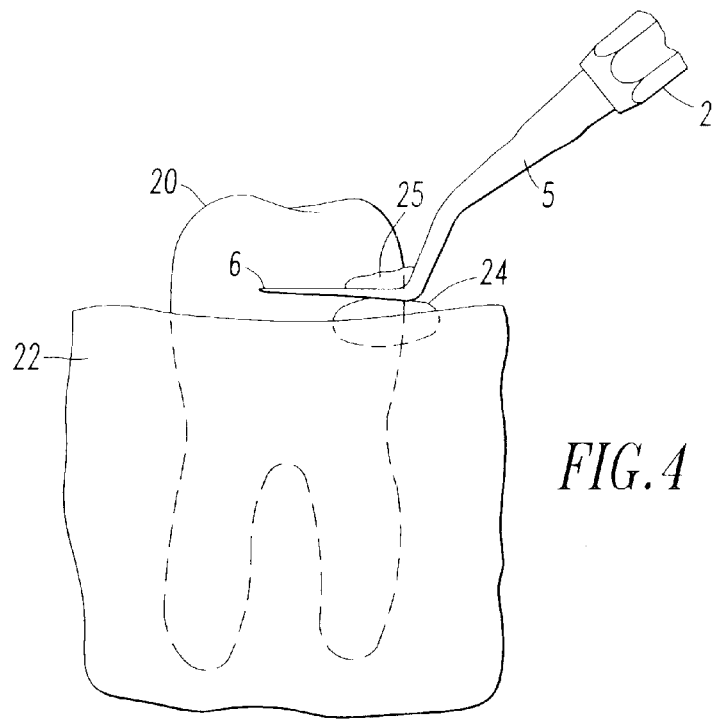
FIG. 4 is a side view of a tooth showing the instrument in position to press material into the periodontal pocket.

Referring to FIGS. 1, 2 and 3 a present preferred embodiment of my hand dental instrument 1 has a generally cylindrical handle 2 and a tip or blade 6 at one or both ends. Like many dental hand instruments the handle has a central portion 3 having a hexagonal cross section and tapered end sections 4 that lead to a cylindrical shank 5. A foot shaped blade 6 is attached to the shank. I prefer that the angle A between the blade 6 and the shank 5 be 120°, but that angle could be an angle of from 110° to 130°. The angle B between the shank 5 and the tapered portion 4 of the handle 2 could be an angle of from 140° to 160° but preferably is 150°. These angles allow unlimited positioning of the blade 6 about a 360° operating axis to enable the user to reach all areas of the mouth with the instrument. The blade has a top surface 7 and a bottom surface 8. The shape of these surfaces is defined by five edge portions identified as the ankle edge 11, heel edge 12, arch edge 13, toe edge 14 and instep edge 15. The ankle, arch and instep edges curve inward and preferably have different depths and curvature. If desired the ankle edge 11 could be straight rather than curve inward. In a present preferred embodiment the length of the blade L is 0.4 inches, the height H is 0.2 inches and the blade thickness is 0.025 inches for the anterior two thirds of the blade containing the toe and 0.035 inches for the remaining one third of the blade comprising the heel. The added thickness in the heel supplies additional strength to prevent warping if dropped or from hard handling during sterilization. The two thicknesses were selected to perform two important functions. The first function is placing the thin gauze into the 1–1.5 mm created space between the tooth and gingiva. The second use is pushing thin gauze strips between the teeth from the buccal to the lingual (from the cheek side to the tongue side) through the interproximal area (the space between the teeth where the triangle of gum fills in) and below the contact point (the point where teeth touch). The space is limited in the anterior area where the teeth are nearly parallel. This anterior limited space determines the maximum thickness of the forward two thirds of the foot.

The gauze must be placed to fill in the entire interproximal created space. The width of the molars from buccal to lingual (check side to tongue side) determines this length of the anterior portion of the blade. Molars are approximately 0.4 inches wide, with embrasures (the space between the rounded sides of the molars) that permit the placement of a 0.3 inch foot completely between the molars. The relatively large space of the embrasures allows the length of the foot to be less than the approximate width of the molars. Consequently, the length of the foot is chosen to be 0.4 inches. Since the shank has a diameter S of 0.1 inches, the top of the foot is 0.3 inches. The 0.3 inches is a sufficient length to carry the gauze strips from the buccal to the lingual. A shorter toe leaves gauze halfway between the teeth and the gauze forms a wad. This results in some of the pocket around the tooth not having gauze applying pressure to stop bleeding and to distend the gums.

The toe 14 has a top edge and a bottom edge that meet at rounded tip 16. If these two edges were extended as indicated by the dotted lines in FIG. 3 they would meet at an angle T of 32°. A blunt edge easily captures and pushes the gauze during placement and does not cut the gauze nor gingiva. The taper allows easy access to a 1–1.5 mm bur abrasion space created between the tooth and gingiva. A second use for the taper is to manipulate dental periodontal structure regeneration material placed in the periodontal pocket to treat periodontal disease. The taper conforms to the interproximal space or embrasure space (space between the rounded sides of teeth). Where advanced periodontal damage causes spaces greater than 1–1.5 mm, the taper allow easy placement of paste in these spaces. Removal of excess paste interproximal is facilitated with this design feature. Other materials used in dentistry are easily manipulated with this taper. The toe has a maximum height of 0.110 inches. The distance from the contact point to the level of gingiva or bone is the limiting dimension. This dimension should be no more than 0.110 inches to allow the instrument to transcend the restrictive interproximal areas between anterior teeth, or areas with minimal periodontal structure destruction.

The blade is angled relative to the shank. As indicated in FIG. 3 there is an angle U between the centerline of the shank and a line perpendicular to a line tangent to the bottom of the foot-shaped blade. This angle should be between 5° and 30°.

There are three types of teeth in the human mouth, incisors, bicuspids and molars. The sides of all the teeth are curved but the curvature differs among these different types of teeth. The sides of molars have a flatter curvature than the sides of incisors and bicuspids. For that reason the curved edges of my instrument generally correspond to the curved sides of the various teeth. The arch edge 13 has a length J and the smallest concavity so that this edge generally corresponds and adapts to the anterior teeth. The ankle edge 11 has the greatest concavity allowing for placement or removal of excess paste from the distal surface of the molars. The instep edge 15 has an intermediate concavity and has use in intermediate spaces.

Figure 5:
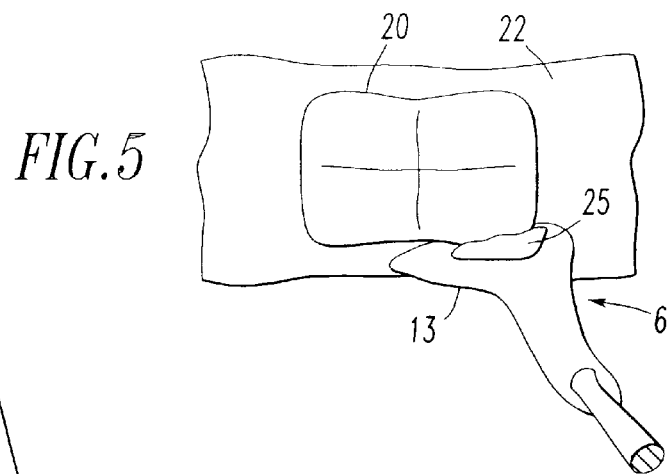
FIG. 5 is a top view of the tooth and instrument shown in FIG. 4.
Figure 6:
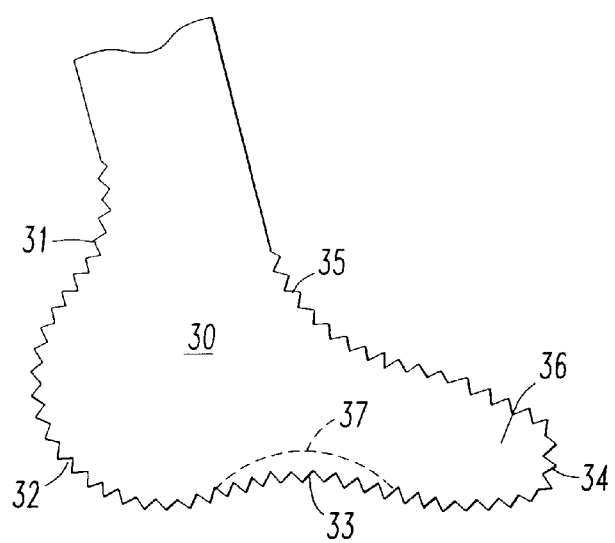
FIG. 6 is an end similar to FIG. 2 showing a second present preferred embodiment of my dental instrument.

One use of the embodiment shown in FIGS. 1, 2 and 3 is shown in FIGS. 5 and 6. In those figures a paste material 24 has been packed between a tooth 20 and adjacent gum tissue 22. Excess material 25 is easily removed because the curvature of the arch edge 13, positioned adjacent the side of the tooth, corresponds to the curvature of the tooth.

The heel 12 preferably is an arc from a circle 0.15 inches in diameter. This shape allows easy gauze capture during placement especially in the wider embrasures found on molars. The curved toe 14 can be used to pack gauze or other material into a periodontal pocket without cutting either the gauze or gum tissue.

A second present preferred embodiment shown in FIG. 6 is similar to the first embodiment 1 but has a slightly different blade configuration. When viewed from a distance the second embodiment would appear to be the same as the first embodiment. Both have a generally cylindrical handle and a foot shaped blade at one or both ends. However, the blade 30 of the second preferred embodiment shown in FIG. 6 has a serrated edge. In this embodiment there is a similar ankle edge 31, heel 32, toe 34 and instep edge 35. The arch edge 33 may be serrated rather than being curved and the toe is more blunt with serrations. In a present preferred embodiment the serrations are 0.02 inch apart tip to tip and the valleys are 0.02 inch deep. This instrument is particularly useful in making impressions of teeth for crowns, caps and prosthetics. When such an impression is made retraction cords are used to displace the gums from the tooth prior to taking an impression. Placement of retraction cord requires a blunt end preferable with tiny serrations to grip the cord. The cord is loosely woven and a sharp tip or edge would separate the weave. Therefore, this embodiment has a blunt end 36. The blunt end is approximately 0.30 inch long and 0.025 to 0.035 inch wide. The arch edge may be flat as indicated by dotted line 37 or have serrations as shown that could be used to grip the cord. The valleys between the peaks of the serration are rounded rather than sharp so as not to cut the strings. After the serrations are cut into the instrument, a buffing process is done to round off the points.

The hand dental instrument has been illustrated as having a foot shaped blade at both ends. However, this blade need only be at only one end. The opposite end could have no tip, could have any of the many tips currently offered on hand dental instruments or may even have a mirror. The hand tool preferably is made of stainless steel. However, other metal alloys and some plastics approved for use in hand dental instruments could be used.

Although I have shown and described certain present preferred embodiments of my hand dental,instrument it should be distinctly understood that the invention is not limited thereto but may be variously embodied within the scope of the following claims.

I claim:

1. An instrument comprised of:
   an elongated handle having a first end and a second end; and
   a foot-shaped blade attached to the first end of the handle, the foot shaped blade having
     a top surface;
     a bottom surface, opposite the top surface;
     a heel edge extending from the handle;
     an arch edge extending from the heel edge;
     a toe edge extending from the arch edge, the toe edge forming a V-shape with a rounded point; and an instep edge extending from the toe edge to the handle;

wherein the edges are all between the top surface and the bottom surface, the heel edge has an outwardly curved shape and the arch and instep edges have an inwardly curved shape and the blade has a thickness and a length which enables the blade to be placed between adjacent teeth in a human mouth, which teeth have a buccal side and a lingual side, and the blade, when so placed, will extend from the buccal side to the lingual side.

2. The instrument of claim 1 also comprising a shank portion attached between the blade and the handle.

3. The instrument of claim 2 wherein a centerline passing through the shank intersects a centerline passing through the handle in an angle of from 140° to 160°.

4. The instrument of claim 3 wherein the angle is 150°.

5. The instrument of claim 2 wherein the top surface of the blade intersects a centerline passing through the shank at a blade angle of from 110° to 130°.

6. The instrument of claim 5 wherein the blade angle is 120°.

7. The instrument of claim 2 wherein a centerline through the shank intersects a line normal to a line tangent to edges of the blade adjacent the arch edge at an angle of from 5° to 30°.

8. The instrument of claim 1 wherein the blade has a thickness adjacent the toe edge which is less than a blade thickness adjacent the heel edge.

9. The instrument of claim 1 wherein the blade has a thickness of 0.025 inches adjacent the toe edge and a thickness of 0.035 inches adjacent the heel edge.

10. The instrument of claim 1 also comprising a second blade attached to the second end of the handle.

11. The instrument of claim 10 wherein the second blade is a foot shaped blade having:
   a top surface;
   a bottom surface, opposite the top surface;
   a heel edge extending from the handle;
   an arch edge extending from the heel edge;
   a toe edge extending from the arch edge, the toe edge forming a V-shaped with a rounded point; and
   an instep edge extending from the toe edge to the handle;
   wherein the edges are all between the top surface and the bottom surface, the heel edge has an outwardly curved shape and the arch and instep edges have an inwardly curved shape and the blade has a thickness and a length which enables the blade to be placed between adjacent teeth in a human mouth, which teeth have a buccal side and a lingual side, and the blade, when so placed, will extend from the buccal side to the lingual side.

12. The instrument of claim 1 wherein a toe angle is formed by a first edge and a second edge both extending from the rounded point, such that lines co-linear with the first edge and the second edge intersect at an angle of 32°.

13. The instrument of claim 1 wherein at least one of the toe edge and the arch edge is a serrated edge.

14. The instrument of claim 13 wherein the serrated edge is comprised of a series of peaks separated by rounded valleys.

15. The instrument of claim 1 wherein the blade and the handle are stainless steel.

16. The instrument of claim 1 also comprising an inwardly curving ankle edge between the heel and the handle.

17. A instrument comprised of:
   an elongated handle having a first end and a second end; and
   a foot-shaped blade attached to the first end of the handle, the foot shaped blade having
   a top surface;
   a bottom surface, opposite the top surface;
   a heel shaped edge extending from the handle;
   an arch edge extending from the heel edge;
   a serrated toe edge extending from the arch edge, the toe edge forming a V-shape with a blunt point; and
   an instep edge extending from the toe edge to the handle;
   wherein the edges are all between the top surface and the bottom surface, the heel edge has an outwardly curved shape and the instep edge has an inwardly curved shape and the blade has a thickness and a length which enables the blade to be placed between adjacent teeth in a human mouth, which teeth have a buccal side and a lingual side, and the blade, when so placed, will extend from the buccal side to the lingual side.

18. The instrument of claim 17 wherein the arch edge is serrated.

19. The instrument of claim 17 wherein the arch edge is flat.

* * * * *